United States Patent [19]
Binz et al.

[11] Patent Number: 5,993,742
[45] Date of Patent: Nov. 30, 1999

[54] DEVICE FOR THE ANALYSIS OF LIQUIDS

[75] Inventors: Dieter Binz, Schriesheim; Albrecht Vogel, Stutensee, both of Germany; Brith Claesson, Vaesteras, Sweden; Hubert Braendle, Oberengstringen, Switzerland; Sean Keeping, West Croydon, United Kingdom

[73] Assignee: ABB Patent GmbH, Mannheim, Germany

[21] Appl. No.: 08/899,749

[22] Filed: Jul. 24, 1997

[30] Foreign Application Priority Data

Jul. 24, 1996 [DE] Germany .......................... 196 29 835

[51] Int. Cl.$^6$ ............................ G01N 35/08; B01D 61/28
[52] U.S. Cl. ................................ 422/81; 422/62; 422/63; 422/82.01; 435/287.1; 436/43; 436/62; 436/103; 436/110; 436/127; 436/174; 436/177; 436/179; 436/180
[58] Field of Search ............................. 422/62, 68.1, 79, 422/81, 82.01, 82.03, 101, 63, 104; 436/43, 62, 175, 103, 179, 110, 180, 127, 174, 177; 435/287.1

[56] References Cited

U.S. PATENT DOCUMENTS

| | | | |
|---|---|---|---|
| 3,930,798 | 1/1976 | Schierjott et al. | 422/79 |
| 4,314,969 | 2/1982 | Arthur et al. | 422/68 |
| 5,160,604 | 11/1992 | Nakamura et al. | 210/85 |
| 5,324,666 | 6/1994 | Siepmann et al. | 436/62 |
| 5,807,699 | 9/1998 | Nason et al. | 435/32 |

*Primary Examiner*—Long V. Le
*Attorney, Agent, or Firm*—Herbert L. Lerner; Laurence A. Greenberg

[57] ABSTRACT

A device for the investigation of liquids, in particular of waste water, includes at least one reaction chamber for receiving the liquid to be investigated as well as liquids for analysis from storage containers. The reaction chamber is disposed in a housing while the storage containers are accommodated within the housing or are set up outside. The housing may be positioned in a freely floating manner within the liquid to be investigated or may be set up outside.

15 Claims, 4 Drawing Sheets

DEVICE FOR THE ANALYSIS OF LIQUIDS

BACKGROUND OF THE INVENTION

1. Field of the Invention

The invention relates to a device for the analysis of liquids, in particular waste water.

All of the devices for the determination of a biological oxygen requirement which are already known involve the measurement of oxygen consumption in a water specimen. They may be subdivided into devices using laboratory methods and on-line measurement methods. The laboratory methods are standardized and described in DIN 38409 Part 51. They involve a dilution method by which the content of biologically degradable substances in the water specimen is determined in the laboratory within five days.

A fermentation calorimeter, which measures the heat production of metabolic processes, is also known. For that purpose, the heat production of the material undergoing fermentation is compensated by a corresponding cooling. The rate of cooling which is determined is proportional to the metabolic heat production and thus is also proportional to the metabolic activity of the biomass. However, the expenditure on apparatus is high, and corresponding systems are too costly for use as a process measurement system.

Known enzyme thermistors measure the heat which is produced when an immobilized layer of enzymes reacts with an organic substance. That heat is measured, for example, through the use of two absolute temperature sensors which are situated in an inlet or outlet of the reaction vessel containing the immobilized enzymes.

In an additionally known flow system, a flow takes place through an enzyme column, at the end of which the temperature is determined. In that case, a second system having an uncoated column serves as a reference. In that case too, a signal difference of the signals from the two temperature sensors is a measure of the heat of reaction.

The known devices for the analysis of waste water are essentially based on the determination of the biological oxygen requirement. The other components of waste water, which frequently exhibit toxic properties or, as nutrient substances, influence the metabolism in nature, are disregarded in most cases. A further disadvantage of the known devices resides in that the waste water to be investigated has to be branched off through additional lines from tanks of clarifying plants and conducted to those devices, since those devices require a very large number of supplementary systems for their operation and, moreover, are sensitive to meteorological factors, so that they can be set up and operated only within a building.

SUMMARY OF THE INVENTION

It is accordingly an object of the invention to provide a device for the analysis of liquids, which overcomes the hereinafore-mentioned disadvantages of the heretofore-known devices of this general type, which can be brought directly into contact with a liquid to be investigated, which requires little space and which may be readily transported.

With the foregoing and other objects in view there is provided, in accordance with the invention, a device for the investigation of liquids, in particular of waste water, comprising a housing freely floating within the liquid to be investigated or disposed outside the liquid to be investigated; storage containers disposed in the housing or outside the housing; and at least one reaction chamber surrounded by the housing for receiving liquid to be investigated and analysis liquids from the storage containers.

The device according to the invention is constructed in such a way that on this basis the waste water in clarifying plants can be investigated for its biological oxygen requirement and for components containing pollutants as well as for its content of nutrient substances in a simple manner. Since the device is constructed from microcomponents, it has very small dimensions, because of which it can also be handled easily. The device is capable of floating and can be positioned, for example, directly in the waste water tanks of clarifying plants. Special supply lines for the waste water to be investigated are not necessary. The device is provided with a plurality of reaction chambers, so that it can be used to determine the biological oxygen requirement of the waste water and moreover to determine whether ammonium, nitrate or phosphate are present therein. The analysis can be extended to further components in a simple manner as a result of the use of a relatively large number of reaction chambers, enzymes and/or reagents.

In accordance with another feature of the invention, the at least one reaction chamber includes at least one reaction chamber for determining a biological oxygen requirement and at least one further reaction chamber for determining further components of the liquid to be investigated.

In accordance with a further feature of the invention, there is provided a cassette removably inserted into the housing, the storage containers being chambers integrated in the cassette.

In accordance with an added feature of the invention, the cassette includes chambers for enzymes and/or reagents, calibration solutions, and buffer solutions and at least one filter and/or a membrane.

In accordance with an additional feature of the invention, there is provided a container containing part of at least one of the filter and the membrane immersed in the liquid to be investigated, a metallic grid through which the liquid to be investigated passes into the container, and a rotor installed in the container for maintaining the liquid to be investigated in motion.

In accordance with yet another feature of the invention, the reaction chamber for the determination of the biological oxygen requirement is disposed directly in the housing or within the cassette.

In accordance with yet a further feature of the invention, the at least one further reaction chamber is three further reaction chambers.

In accordance with yet an added feature of the invention, there are provided pumps and supply lines downstream of the filter for feeding the liquid to be investigated from the filter to the at least one reaction chamber.

In accordance with yet a additional feature of the invention, there are provided supply lines, connecting lines and pumps for feeding enzymes and/or reagents, calibration solutions, buffer solutions and pure water to the at least one reaction chamber.

In accordance with again another feature of the invention, there is provided at least one measuring device associated with the at least one reaction chamber.

In accordance with again further feature of the invention, there are provided supply and connecting lines in the housing, and hose-type lines connecting the supply and connecting lines to the storage containers disposed outside the housing.

In accordance with again an added feature of the invention, the storage containers disposed within the housing have a capacity for enzymes and/or reagents, buffer solutions and calibration solutions for at least 9660 investigations, and the at least one reaction chamber has a size of at most 1 cm3.

In accordance with again an additional feature of the invention, there is provided a water processing device for receiving the liquid to be investigated, and a storage container for pure water connected to the water processing device.

In accordance with still another feature of the invention, there is provided a filter device for receiving the liquids derived from the at least one reaction chamber and for branching off the liquid out of the housing to the outside.

In accordance with a concomitant feature of the invention, there is provided a voltage distributor in the housing, a voltage source installed outside the housing and connected to the voltage distributor, transmitter, and at least one microprocessor for controlling the pumps and for storing and transmitting measurement signals of the measuring devices to the transmitter.

Other features which are considered as characteristic for the invention are set forth in the appended claims.

Although the invention is illustrated and described herein as embodied in a device for the analysis of liquids, it is nevertheless not intended to be limited to the details shown, since various modification and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
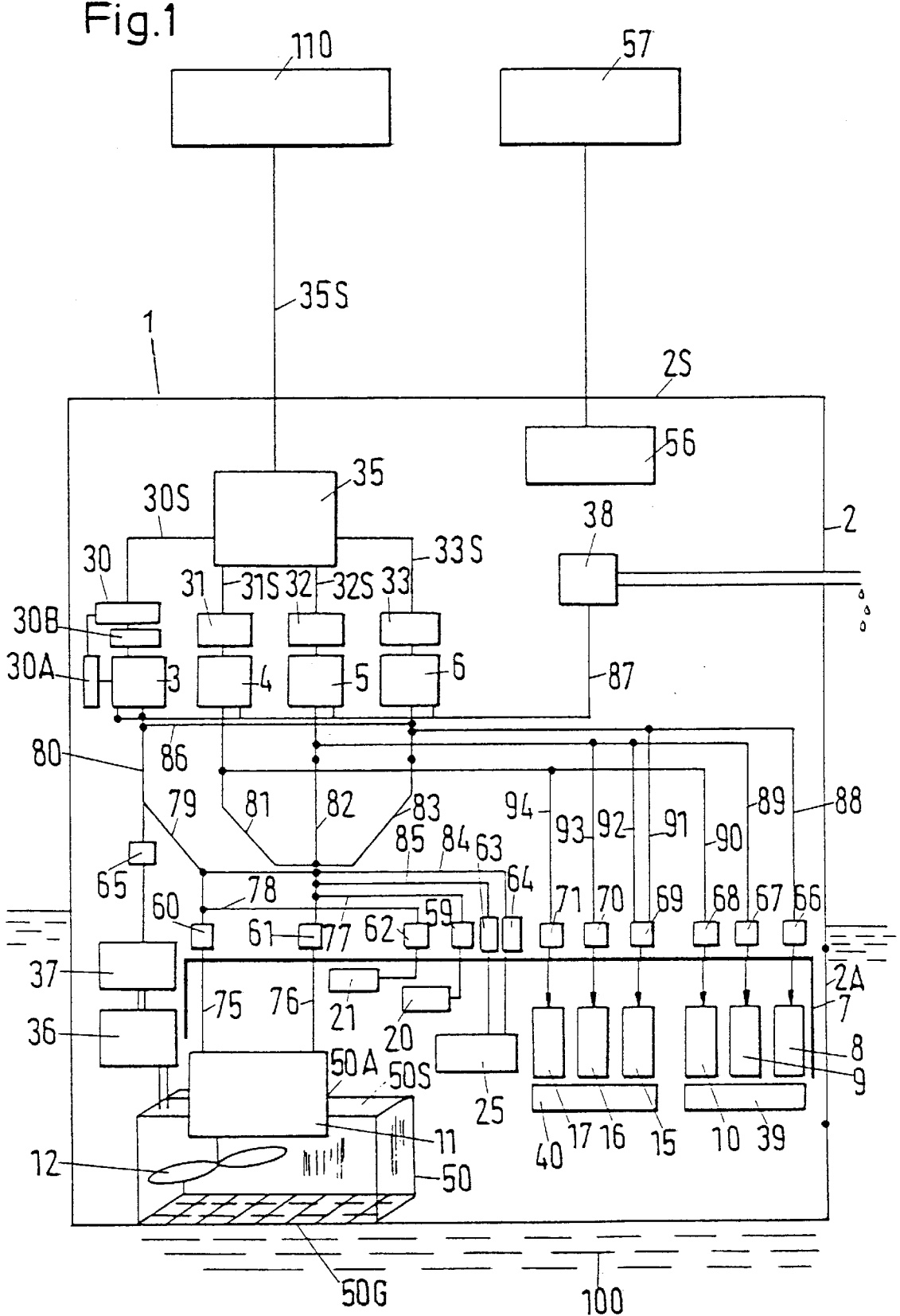
FIG. 1 is a block diagram of a device for the analysis of waste water.

Referring now to the FIGURES of the drawings in detail and first, particularly, to FIG. 1 thereof, there is seen a device 1 which has a housing 2 that is capable of floating, four reaction chambers 3, 4, 5 and 6, a cassette 7 which includes three chambers 8, 9, 10 for enzymes, a filter 11, three chambers 15, 16 and 17 for reagents, two chambers 20 and 21 for calibration solutions as well as a chamber 25 for buffer solution, a rotor 12, four measuring devices 30, 31, 32 and 33, a microprocessor 35, a water processing device 36, a fresh water container 37, a filter device 38, a heating device 39, a cooling device 40 and a voltage distributor 56.

The housing 2 is constructed to be capable of floating and can be directly immersed in a waste water tank of a non-illustrated clarifying plant. Waste water 100 to be investigated is fed through the filter 11, supply lines 75 and 76, two downstream pumps 60 and 61, as well as supply lines 79 and 80 to the reaction chamber 3, a supply line 81 to the reaction chamber 4, a supply line 82 to the reaction chamber 5, and a supply line 83 to the reaction chamber 6. The filter 11 is directly immersed in the waste water 100 for this purpose. It is also possible to use a non-illustrated membrane in place of the filter 11 to draw the waste water 100. A lower end of the housing 2, which is immersed in the waste water 100, is provided with a container 50 in order to draw the waste water 100. As is shown herein, the container 50 has the shape of a cylinder or the shape of a parallelepiped. This container 50 is intended to receive the waste water 100. The container 50 is closed at its top and at its lateral boundary surfaces. The top of the container 50 has an opening 50A, through which a lower end of the filter 11 is passed in such a way that the latter penetrates a few millimeters into the container 50. The bottom of the container 50 is covered by a metal grid 50G. The waste water 100 can flow through this metal grid 5OG into the container 50. The meshes of the metal grid 5OG have such a magnitude that the finest suspended particles pass into the container 50 together with the waste water 100. At the same time, non-illustrated fats are kept away from the filter 11 by the metal grid 50G. The rotor 12 is installed within the container 50 in order to ensure that the filter 11 is not obstructed by small non-illustrated suspended particles. As FIG. 1 shows, the rotor 12 is disposed in such a way as to be somewhat displaced relative to the filter 11, so that its rotor blades move the waste water 100 past the filter 11 at very high speed. The opening 50A is constructed in such a way that only the waste water 100 drawn by the filter 11 and the downstream pumps 60 and 61 can pass into the device 1 and an undesired inflow of larger quantities of waste water 100 is prevented.

Each one of the reaction chambers 3, 4, 5 and 6 shown herein has a volume which is at most 1 cm$^3$. The reaction chamber 3 is intended for the determination of the biological oxygen requirement of the waste water 100. The reaction chamber 3 contains non-illustrated bacteria which are capable of oxidatively converting organic substances contained in the waste water 100. In the course of these aerobic processes, oxygen is consumed and biomass and heat are generated. In order to ensure that the bacteria are not swept away when the reaction chamber 3 is emptied, they are immobilized on non-illustrated substrates. Preferably, use is made of substrates which are shaped as small pearls and are made, for example, from glass. The bacteria are settled in pores of these pearls. Preferably, use is made of two or more substrates, on which different bacteria are settled. By way of example, substrates with bacteria of the strains Rhodococcus Erytropolis and Issatchenkia Orientalis are immobilized in the reaction chamber 3. The pearl-shaped substrates having a diameter of 0.1 mm to 1 mm are held back with the aid of a non-illustrated lattice when the reaction chamber 3 is emptied.

The measuring device 30 is associated with the reaction chamber 3. This measuring device 30 has two electrochemically operating sensors 30A and 30B, with which the oxygen content in the waste water 100 can be measured. The first sensor 30A is disposed in such a way that it measures the oxygen content of the waste water 100 which is just flowing into the reaction chamber 3. After the filling of a defined quantity of less than 1 cm$^3$ of waste water 100, for example, the reaction chamber 3 is filled up with buffer solution from the container 25. The buffer solution is fed to the reaction chamber 3 through the supply lines 79, 80 and 84 through the use of a pump 64. In this connection, distilled water or a borate buffer is used as the buffer solution. The reaction chambers 4, 5 and 6 can also be supplied with this buffer solution from a pump 63 through the supply lines 85 and 81 leading to the reaction chamber 4, the supply lines 85 and 82 leading to the reaction chamber 5 and the supply lines 85 and 83 leading to the reaction chamber 6. The second sensor 30B is installed in such a way that it can measure the oxygen content of the waste water 100 after the bacteria have converted the organic substances contained therein into biomass and heat and have consumed oxygen in the process. The quantity of organic substances in the waste water 100 can be determined from the quantity of oxygen which is consumed. In place of the measuring device 30 described herein, it is also possible to use an optically operating measuring device or any other measuring device suitable for this purpose.

After each measurement, the reaction chamber 3 is rinsed with pure water. This also applies to the three other reaction chambers 4, 5 and 6. This water is obtained by the water processing device 36 from the waste water 100 and is stored in the container 37. The structure of the water processing device 36 is already included in the prior art and is therefore not explained in greater detail herein. The water is fed from the container 37 with the aid of a pump 65 through the lines 80 and 86 to the reaction chambers 3, 4, 5 and 6. In place of a rinsing with pure water, the reaction chambers 3, 4, 5 and 6 can also be rinsed with the waste water 100 which is fed from the filter 11 through the lines 75, 76, 79, 80, 81, 82 and 83 through the use of the pumps 60 and 61. The liquids which are exhausted from the reaction chambers 3, 4, 5 and 6 are fed through a line 87 to the filter device 38 and from there to the non-illustrated clarifying plant.

Measurement signals of the measuring device 30 are transmitted to the microprocessor 35. For this purpose, the measuring device 30 is connected through a signal line 30S to a signal input of the microprocessor 35. There, the measurement signals are stored and transmitted to a transmitter 110 which is installed outside the device 1 at a non-illustrated observation station. As is shown in FIG. 1, the microprocessor 35 can be connected to the transmitter 110 through a signal line 35S. However, it is also possible to transmit the measurement signals by using a non-illustrated sender. The measurement signals are evaluated and displayed with the aid of the transmitter 110. Furthermore, the microprocessor 35 stores programs according to which the microprocessor 35 controls all of the pumps of the device 1 so that the reaction chambers 3, 4, 5 and 6 are always supplied with the required liquids at the correct time.

Besides the reaction chamber 3, the reaction chambers 4, 5 and 6 are also intended for the analysis of the waste water 100. The measuring devices 31, 32 and 33 which are each associated with a respective one of these reaction chambers 4, 5 and 6 supply measurement signals that can each be fed to the microprocessor 35 through one respective signal line 31S, 32S and 33S. The detection of each of ammonium, nitrate and phosphate takes place in a respective one of the reaction chambers 4, 5 and 6, with the aid of enzymes and reagents. In this connection, the reaction chamber 4 is used for the detection of phosphate, while the analysis of the waste water 100 for its content of ammonium takes place in the reaction chamber 5. The waste water 100 is tested in the reaction chamber 6 for its nitrate content. The enzymes in the form of nitrate reductase, glutamate dehydrogenase and pyruvate oxidase are each contained in a respective one of the chambers 8, 9 and 10, while reagents in the form of NADH, alpha-ketoglutarate and pyruvate are each filled into a respective one of the chambers 15, 16 and 17.

As FIG. 1 shows, the chambers 8, 9, 10, 15, 16, 17, 20, 21 and 25 as well as the filter 11 belong to the cassette 7. The cassette 7 is constructed in such a way that it can be removed at any time from the housing 2 through an opening 2A in the housing 2 that can be closed in a water-tight manner, and the cassette 7 can be replaced with another one. Such an exchange preferably takes place every three months, since the contents of the chambers 8, 9, 10, 15, 16, 17, 20, 21 and 25 are portioned precisely in such a way that they are sufficient for approximately 100 days or 9660 investigations, if it is assumed that four measurements are carried out each hour. The capacities of the chambers 8, 9 and 10 for the enzymes amount to 26 ml, 1.1 ml and 0.2 ml. The chambers 15, 16 and 17 for the reagents have capacities of 4.2 ml, 1.3 ml and 0.1 ml. The chambers 8, 9, 10, 15, 16, 17, 20, 21 and 25 of the cassette 7 are provided with non-illustrated connecting elements for the supply lines 75 to 94, so that a simple release or connection is possible. In place of this cassette 7, all of the supply lines may also be connected through non-illustrated hose-type connecting lines to non-illustrated storage containers, which are set up outside the housing 2 on a firm base. For this eventuality, the housing 2 is provided with non-illustrated openings which can be closed in a water-tight manner, for the passage of the hose-type connecting lines.

The connection of the reaction chambers 4, 5 and 6 with the chambers 8, 9, 10, 15, 16 and 17 takes place through supply lines and connecting lines. As FIG. 1 shows, the reaction chamber 6 is connected through a supply line 88 to the chamber 8, while the reaction chamber 5 is connected through a supply line 89 to the chamber 9. The reaction chamber 4 is connected through a supply line 90 to the chamber 10. A respective pump 66, 67 and 68 is incorporated into each of the supply lines 88, 89 and 90. The chamber 15 is connected through a first connecting line 91 to the supply line 88 of the reaction chamber 6. The chamber 15 is connected through a second connecting line 92 to the reaction chamber 5. The chamber 16 is also connected through a third connecting line 93 to the reaction chamber 5. The chamber 17 is connected through a fourth connecting line 94 to the reaction chamber 4. Pumps 69, 70 and 71 are each connected downstream of a respective one of the chambers 15, 16 and 17.

Furthermore, the first chamber 20 containing calibration solution is connected through the supply lines 77 and 81 to the reaction chamber 4, through the supply lines 77 and 82 to the reaction chamber 5 and through the supply lines 77 and 83 to the reaction chamber 6. A second chamber 21, which likewise contains calibration solution, is connected through the supply lines 78, 79 and 80 to the reaction chamber 3. In each case one respective pump 59 and 62 is connected downstream of the two chambers 20 and 21.

In order to provide for the transport of all liquids which are required for the analysis, it is also possible to use non-illustrated supply lines which have a non-illustrated capillary structure internally, in place of the above-described supply lines and connecting lines 77 to 94 and the pumps 60 to 71. The control of the quantities of liquid to be transported to the reaction chambers 3, 4, 5 and 6 can take place with the aid of non-illustrated valves, which are incorporated in these supply lines and are driven by the microprocessor 35.

The calibration solution in the chamber 20 serves for the performance of a calibration of the measuring devices 31, 32 and 33 for ammonium, nitrate and phosphate at regular intervals, preferably once per day. It includes an aqueous solution which contains precisely known concentrations of nitrate, ammonium and phosphate, preferably at the upper end of the desired range of measurement of 100 mg/l. In order to calibrate the measuring devices 31, 32 and 33, the calibration solution is passed into the reaction chambers 4, 5 and 6 in the calibration cycle in place of the waste water. The values for nitrate, ammonium and phosphate which are determined by the measuring devices 31, 32 and 33 are compared with the known concentration in the microprocessor 35 and stored. Subsequent measurements are then appropriately corrected.

The calibration solution 21 serves for the performance of a calibration of the measuring device 30 for the biological oxygen requirement at regular intervals, preferably once per day. It includes a buffered aqueous solution having a precisely defined content of glucose or a precisely known mixture of glucose and glutamic acid, and has a precisely defined proportion of a biological oxygen requirement, which is preferably between 200 and 500 mg/l. In order to calibrate the measuring device 30, the calibration solution is passed into the reaction chamber 3 in the calibration cycle in place of the waste water 100. The value for the biological oxygen requirement which is determined by the measuring device 30 is compared with the known concentration in the microprocessor 35 and stored. Subsequent measurements are then appropriately corrected.

In order to ensure that the enzymes and reagents are always exposed to the temperatures which are necessary for their preservation, the heating device 39 is associated with the chambers 8, 9 and 10 and the cooling device 40 is associated with the chambers 15, 16 and 17.

In order to provide for the detection of nitrate in the case of an assumed maximum concentration of 100 mg/l nitrate in the waste water 100, 10 μl of waste water 100 are pumped into the reaction chamber 6. Subsequently, 0.1 μl of nitrate reductase from the chamber 8, which is stored therein in a concentration of 10 mg/l, and 5.3 μl of NADH from the chamber 15, which is stored therein in a concentration of 1.6 mmol/l, are introduced into the reaction chamber 6.

If nitrate is contained in the waste water, the following reaction proceeds:

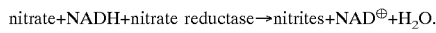
nitrate+NADH+nitrate reductase→nitrites+NAD⊕+H₂O.

It is possible to detect NAD⊕ and thus the existence of nitrate in the waste water with the aid of the measuring device 33, which in this case is constructed from thick layer sensors.

The detection of ammonium is carried out in the reaction chamber 5. In the first instance, 10 μl of waste water 100, 0.14 μl of alpha-ketoglutarate in a concentration of 50 mg/l and 0.13 μl of glutamate dehydrogenase in a concentration of 10 mg/l are again pumped into the reaction chamber 5. If ammonium is contained in the waste water 100, the following reaction proceeds therein:

ammonium+NADH+alpha-ketoglutarate+glutamate dehydrogenase→L-glutamate+NAD⊕

It is possible to detect NAD⊕ and thus the existence of nitrate in the waste water with the aid of the measuring device 32, which is also constructed from thick layer sensors.

The detection of phosphate takes place in the reaction chamber 4. After the filling of 10 μl of waste water 100, 0.001 μl of pyruvate in a concentration of 1 mol/l and 0.02 μl of pyruvate oxidase in a concentration of 110 mg/l, the following reaction proceeds in the reaction chamber 4, assuming that phosphate is contained in the waste water 100:

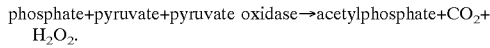
phosphate+pyruvate+pyruvate oxidase→acetylphosphate+CO₂+H₂O₂.

H₂O₂ and thus phosphate in the waste water are detected with the aid of the measuring device 31, which is constructed in a similar way to the measuring device 33.

The measurement signals of the measuring devices 31, 32 and 33 are transmitted to the microprocessor 35 and from there to the transmitter 110 for evaluation.

The existence of nitrate, ammonium and phosphate in the waste water 100 can also be detected exclusively with reagents. In this case, use is then preferably made of those which cause a coloration of the liquids contained in the reaction chambers 4, 5 and 6 when nitrate, ammonium or phosphate is contained in the waste water 100. In this case, use is made of optically operating measuring devices 31, 32 and 33. In place of the measuring devices described herein, it is also possible to use all other devices of this type, if they satisfy the requirements appertaining to these measurements.

After each measurement, the reaction chambers 4, 5 and 6 are rinsed with pure water from the container 37 or with waste water from the filter 11. The time intervals at which the analyses are carried out are controlled in the microprocessor. The microprocessor controls all of the pumps 60 to 71 which are connected through non-illustrated signal lines to the microprocessor 35 for this purpose. The voltage distributor 56 is provided in order to furnish the electrical supply. The voltage distributor 56 receives the electrical voltage of a voltage source 57, which is disposed outside the housing 2. The rotor 12, the microprocessor 35, the heating device 39 and the cooling device 40 as well as the pumps 59 to 71 are connected to the voltage distributor 57. In place of an external voltage source 57, it is also possible to place non-illustrated photoelectrochemical cells on a surface 2S of the housing 2. The required voltage can then be supplied from the cells.

Figure 2:
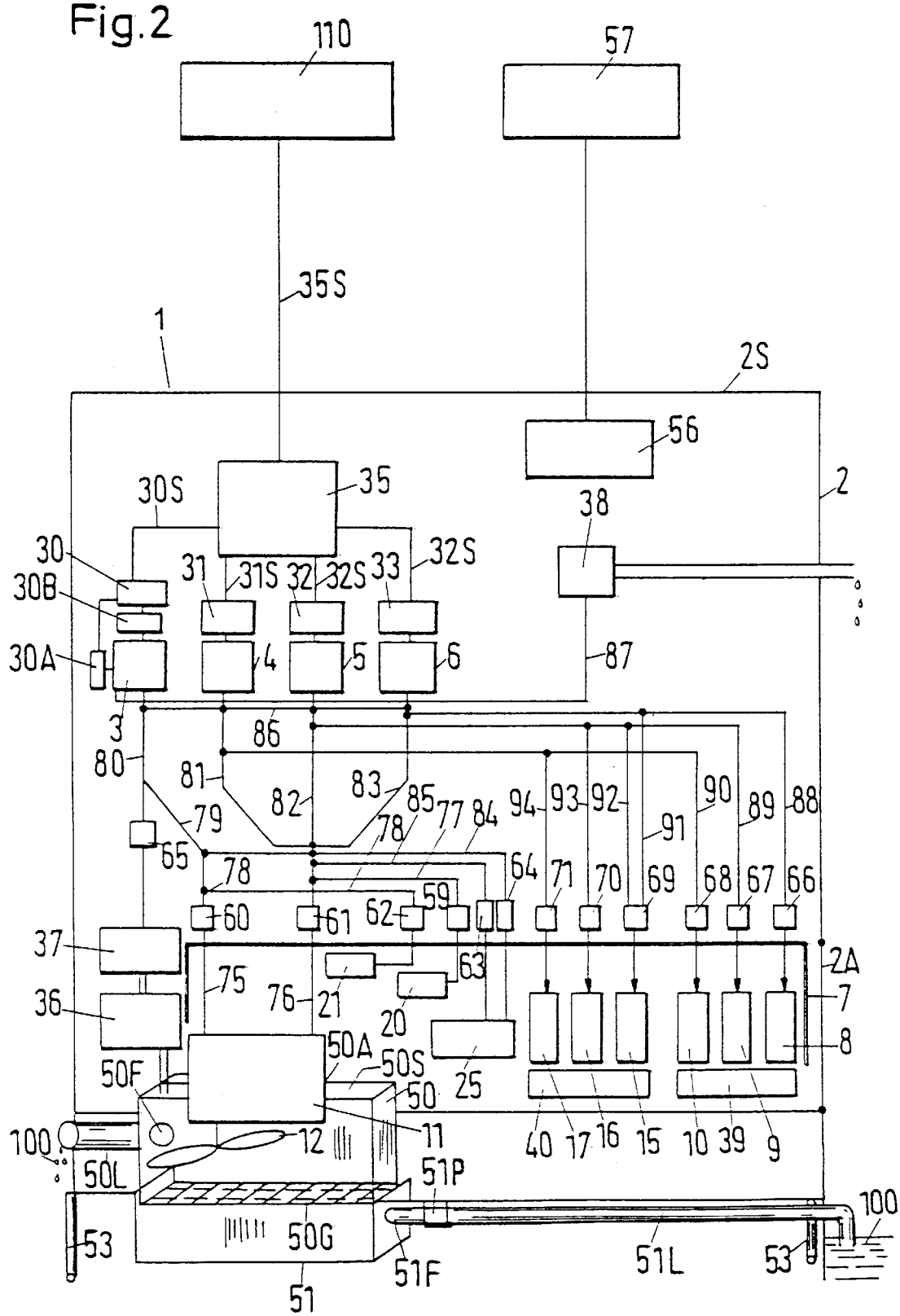
FIG. 2 is a block diagram of a variant of the device shown in FIG. 1.

FIG. 2 shows a variant of the device 1 shown in FIG. 1. The two devices have almost the same construction. Accordingly, identical components are provided with the same reference symbols. The sole difference between the two devices 1 resides in that the device 1 according to FIG. 2 can be operated and disposed outside the liquid to be investigated. For this purpose, a tub-shaped component 51 of the same cross-section is placed against the bottom of the container 50 and is connected in a water-tight manner to the container 50. The component 51 is provided at one side with an opening 51F, to which a line 51L is connected. An upper region of a side of the container 50 which lies opposite the opening 51F likewise has an opening 50F, to which a line 50L is also connected. A pump 51P is integrated into the line 51L. Waste water 100 is drawn through the line 51L from a tank of a non-illustrated clarifying plant. The conveying capacity of the pump 51P is dimensioned in such a way that the container 50 is always filled with waste water 100 up to its upper edge 50S, so that the region of the filter 11 which projects into the container 50 is immersed in the waste water 100. The waste water 100 which is not required flows through the line 50L out of the container 50 again and back into the non-illustrated clarifying plant. Additional supporting elements 53, which are secured to the bottom of an edge region of the housing 2, increase the stability of the device on a non-illustrated firm base.

Figure 3:
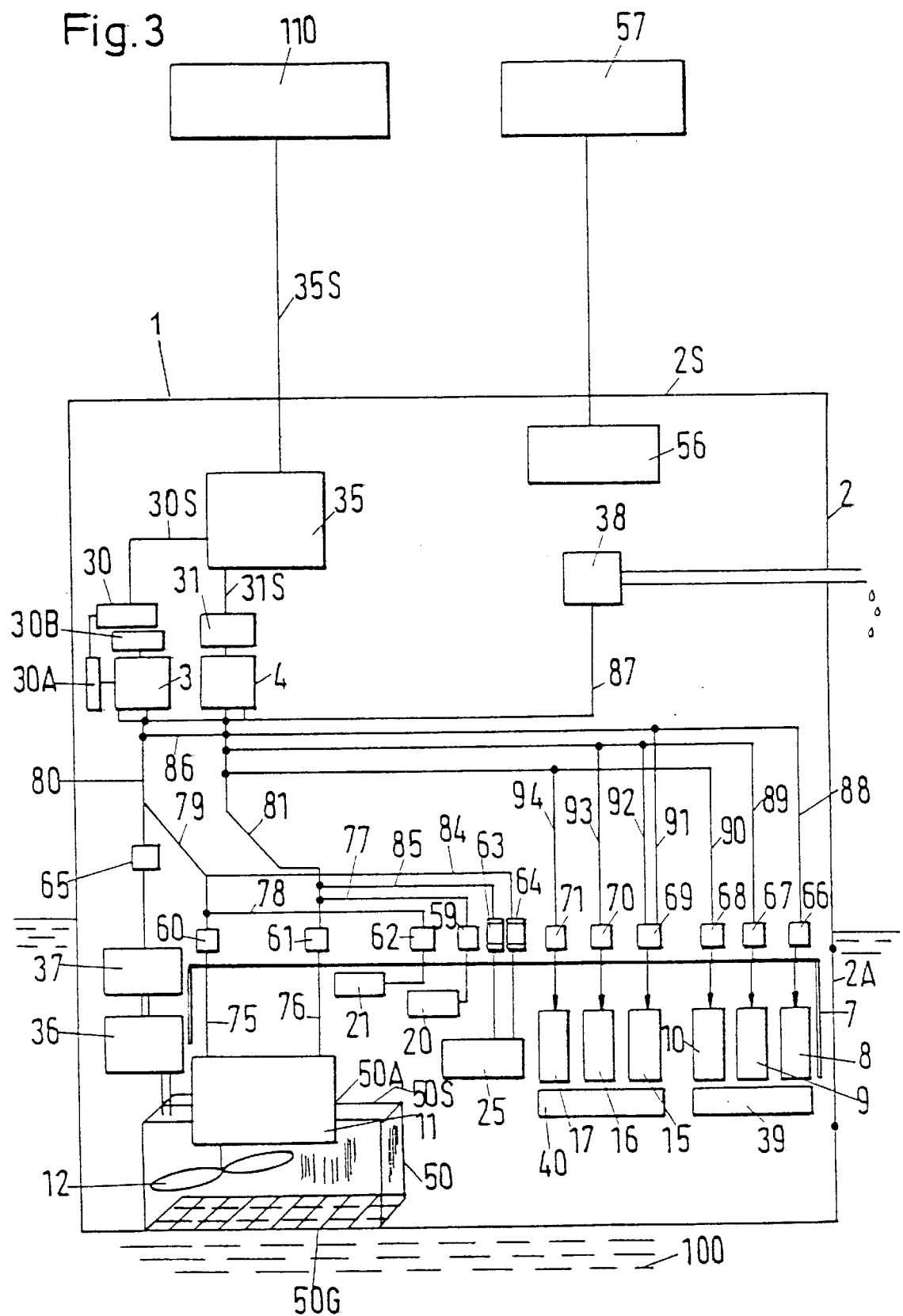
FIG. 3 is a block diagram of a simplified embodiment of the device according to FIG. 1.

FIG. 3 shows a simplified device 1 which, however, at its core corresponds with the device 1 according to FIG. 1. Accordingly, in this case as well, identical components are provided with the same reference symbols. The difference merely resides in that besides the reaction chamber 3 for the determination of the biological oxygen requirement, only one further reaction chamber 4 is provided. The waste water 100 is successively investigated for nitrate, ammonium and phosphate in the reaction chamber 4. After each analysis, in the first instance the reaction chamber 4 is rinsed with pure water or with waste water. In the case of the embodiment shown in FIG. 3, the reaction chamber 4 is therefore connected to all of the storage containers 8, 9, 10 as well as 15, 16, 17 for the enzymes and reagents, through the supply lines and connecting lines 88 to 94. In this case as well, the pumps 66 to 71 are incorporated in all of the supply lines 88 to 94. The temporally correctly coordinated supply of the waste water 100, of the enzymes, reagents, buffer solutions, calibration solutions and pure water is controlled from the microprocessor 35, which actuates the pumps in accordance with a program that is stored therein.

Figure 4:
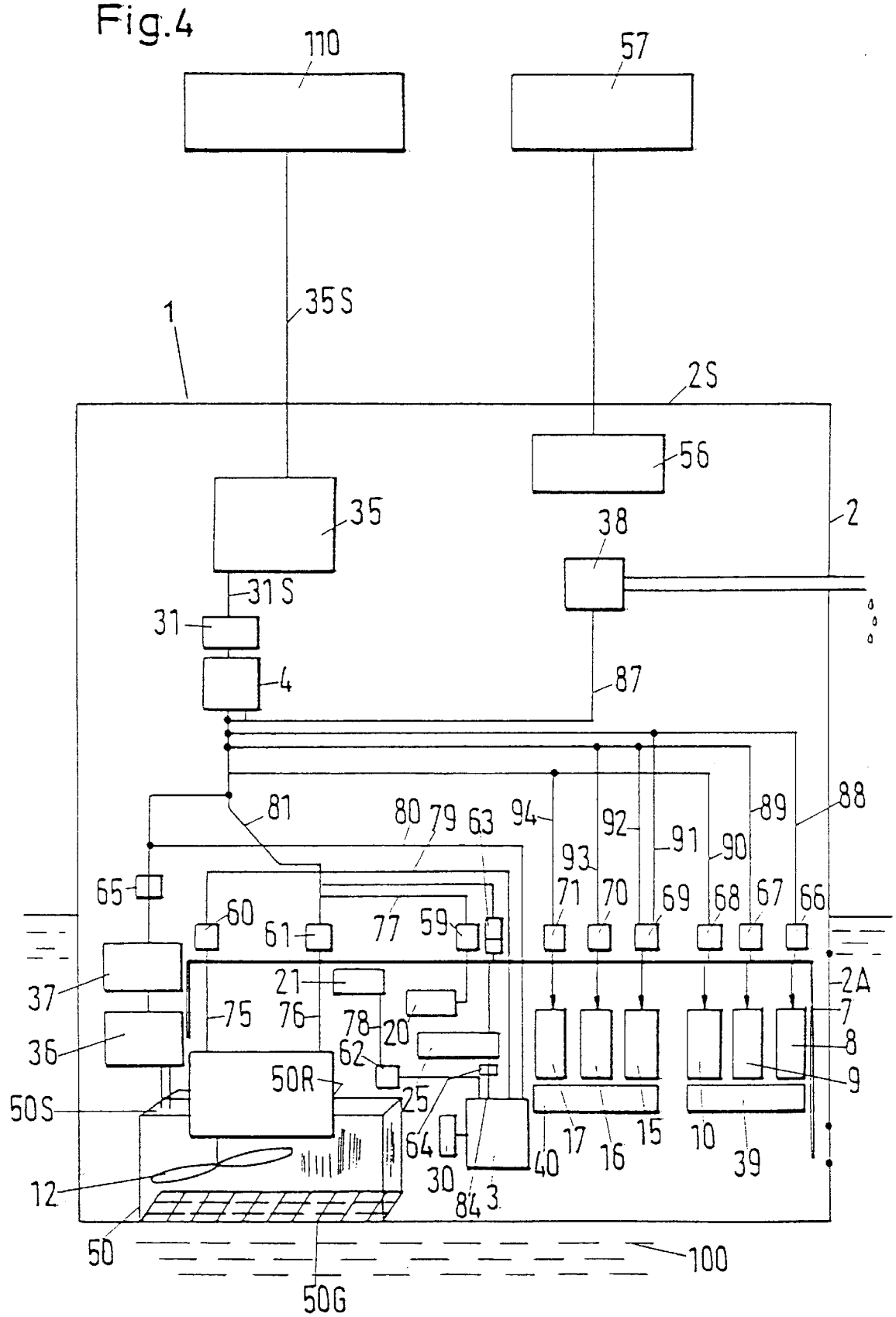
FIG. 4 is a block diagram of a variant of the embodiment shown in FIG. 3.

The device 1 shown in FIG. 4 differs from the embodiment according to FIG. 3 only in that the reaction chamber 3 for the determination of the biological oxygen requirement is disposed in the cassette 7. This has the advantage of also exchanging the reaction chamber 3 upon each change of the cassette 7. This ensures that after approximately 100 days, the non-illustrated bacteria in the reaction chamber 3 are renewed. Thus, the reliability of the measurements is improved. In this case as well, as in the case of all of the other embodiments, the waste water 100 is fed to the reaction chamber 3 through the supply lines 75 and 79 with the aid of the pump 60. The connection to the container 37 containing pure water is effected through the supply line 80. The buffer solution from the chamber 25 is fed through the supply line 84 and the pump 64 and the calibration solution from the chamber 21 is fed, in the same way as in the case of all of the other embodiments, through the supply line 78 and the pump 62. The measuring device 30, which is associated with the reaction chamber 3, in this case is also connected to the microprocessor 35 through a non-illustrated signal line. The herein-described configuration of the reaction chamber 3 in the cassette 7 is also possible in the case of all of the above-described embodiments.

We claim:

1. A device for the investigation of a liquid, comprising:
   a housing including:
   a first enclosure defining a first reaction chamber receiving a portion of a liquid when said first reaction chamber is communicating with the liquid, and a first measuring device operatively associated with said first reaction chamber for generating a measurement signal indicating an oxygen content of the liquid;
   a second enclosure defining a second reaction chamber receiving a portion of the liquid when said second reaction chamber is communicating with the liquid, and a second measuring device operatively associated with said second reaction chamber for generating a measurement signal indicating an amount of ammonium contained in the liquid;
   a third enclosure defining a third reaction chamber receiving a portion of the liquid when said third reaction chamber is communicating with the liquid, and a third measuring device operatively associated with said third reaction chamber for generating a measurement signal indicating an amount of nitrate contained in the liquid;
   a fourth enclosure defining a fourth reaction chamber receiving a portion of the liquid when said fourth reaction chamber is communicating with the liquid, and a fourth measuring device operatively associated with said fourth reaction chamber for generating a measurement signal indicating an amount of phosphate contained in the liquid;
   lines supplying said second, third, and fourth reaction chambers with a substance selected from the group consisting of an enzyme, a reagent, a calibration solution, and a buffer solution; and
   at least one line supplying said first reaction chamber with a substance selected from the group consisting of a calibration solution and a buffer solution.

2. The device according to claim 1, wherein said housing is constructed to float.

3. The device according to claim 1, including a cassette removably insertable into said housing, said cassette having:
   storage containers for holding at least one reagent, at least one enzyme, at least one calibration solution, and at least one buffer solution;
   an entry container;
   a filter, at least a part of said filter disposed in said entry container, said filter receiving the liquid and communicating with said reaction chambers;
   a grid connected to said entry container, said grid for allowing the liquid to pass therethrough to said filter; and
   a rotor disposed between said grid and said filter, said rotor for maintaining the liquid in motion.

4. The device according to claim 3, wherein said first enclosure and said first measuring device are disposed within said cassette.

5. The device according to claim 3, wherein said storage containers are dimensioned to have a capacity enabling at least 9660 investigations, and said reaction chambers have a size that is at most 1 $cm^{3}$.

6. The device according to claim 1, wherein said housing includes:
   an entry container;
   a filter, at least a part of said filter disposed in said container, said filter receiving the liquid and communicating with said reaction chambers;
   a grid connected to said container, said grid for allowing the liquid to pass therethrough to said filter;
   a rotor disposed between said grid and said filter, said rotor for maintaining the liquid in motion.

7. The device according to claim 1, wherein said lines communicate with storage containers disposed externally from said housing.

8. The device according to claim 1, wherein the liquid is water and including:
   a water processing device for receiving and purifying the water; and
   a container communicating with said water processing device for storing the purified water.

9. The device according to claim 1, including a filter device communicating with said reaction chambers, said filter device for receiving, filtering and externally disposing of the liquid.

10. The device according to claim 1, including pumps controlling a supply of the substances to said reaction chambers;
    a microprocessor receiving said measurement signals from said measuring devices and storing said measurement signals; and
    a voltage distributor for connection to an external voltage supply and for supplying voltage to said pumps and said microprocessor.

11. The device according to claim 10, including a transmitter for transmitting said measurement signals.

12. A device for the investigation of a liquid, comprising:

a first enclosure defining a first reaction chamber receiving a portion of a liquid when said first reaction chamber is communicating with the liquid, and a first measuring device operatively associated with said first reaction chamber for generating a measurement signal indicating an oxygen content of the liquid, said first reaction chamber including bacteria capable of oxidatingly converting organic substances;

a second enclosure defining a second reaction chamber receiving a portion of the liquid when said second reaction chamber is communicating with the liquid, and a second measuring device operatively associated with said second reaction chamber for generating a measurement signal indicating an amount of another substance contained in the liquid.

13. The device according to claim 12, wherein said first reaction chamber receives an unaltered portion of the liquid.

14. The device according to claim 13, wherein said first and second reaction chambers and said first and second measuring devices are disposed within a floatable housing.

15. The device according to claim 14, including a transmitter for transmitting said measurement signals.

* * * * *